(12) United States Patent
Wu

(10) Patent No.: US 8,740,831 B2
(45) Date of Patent: Jun. 3, 2014

(54) WIPER AND THE PREPARING METHOD THEREOF

(75) Inventor: Zhendong Wu, Mentougou (CN)

(73) Assignee: Longood Medicine (Jiangsu) Co., Ltd., Lianyungang (CN)

( * ) Notice: Subject to any disclaimer, the term of this patent is extended or adjusted under 35 U.S.C. 154(b) by 1469 days.

(21) Appl. No.: 10/584,488

(22) PCT Filed: Dec. 14, 2004

(86) PCT No.: PCT/CN2004/001453
§ 371 (c)(1),
(2), (4) Date: Apr. 13, 2007

(87) PCT Pub. No.: WO2005/060905
PCT Pub. Date: Jul. 7, 2005

(65) Prior Publication Data
US 2008/0119776 A1 May 22, 2008

(30) Foreign Application Priority Data

Dec. 23, 2003 (CN) .......................... 2003 1 0121777
Dec. 23, 2003 (CN) .......................... 2003 1 0121778

(51) Int. Cl.
*A61M 35/00* (2006.01)
*A61F 13/38* (2006.01)
*A45D 34/04* (2006.01)
*A45D 40/26* (2006.01)

(52) U.S. Cl.
CPC .............. *A61M 35/006* (2013.01); *A61F 13/38* (2013.01); *A45D 34/042* (2013.01); *A45D 34/045* (2013.01); *A45D 34/046* (2013.01); *A45D 40/262* (2013.01); *A45D 40/264* (2013.01); *A45D 40/265* (2013.01); *A45D 40/267* (2013.01)
USPC .......... 604/3; 604/1; 604/2; 206/209; 206/361

(58) Field of Classification Search
CPC ............ A45D 40/0087; A45D 34/042; A45D 34/043; A45D 34/045; A45D 34/046; A45D 34/048; A45D 34/02; A45D 40/262; A45D 40/264; A45D 40/265; A45D 40/267; A45D 44/18; A61M 35/006; A61F 13/38; C12M 23/32
USPC .............. 604/317, 318, 319, 93.01, 315, 313, 604/540, 77, 35, 131; 15/320, 341, 347, 15/409; 228/20.5; 43/110, 111, 133; 132/317, 318; 401/118, 119, 126, 127, 401/128, 129, 130
See application file for complete search history.

(56) References Cited

U.S. PATENT DOCUMENTS

| | | | |
|---|---|---|---|
| 1,573,648 A * | 2/1926 | Sheely | 604/1 |
| 2,902,146 A | 9/1959 | Doherty | |
| 3,792,699 A * | 2/1974 | Tobin et al. | 600/572 |
| 3,818,911 A * | 6/1974 | Fournier | 604/1 |
| 3,923,604 A * | 12/1975 | Monaghan | 600/572 |
| 4,206,843 A * | 6/1980 | Rainey | 206/216 |
| 4,211,323 A * | 7/1980 | Olsen | 206/210 |
| 4,387,725 A * | 6/1983 | Mull | 600/572 |
| 4,586,604 A | 5/1986 | Alter | |
| 4,600,328 A * | 7/1986 | Clements | 401/129 |
| 4,657,869 A * | 4/1987 | Richards et al. | 435/287.6 |
| 4,707,450 A * | 11/1987 | Nason | 600/572 |
| 4,711,354 A * | 12/1987 | Bennett | 206/385 |
| 4,733,784 A * | 3/1988 | Bennett | 215/49 |
| 4,747,719 A * | 5/1988 | Parkin | 401/132 |
| 4,903,708 A | 2/1990 | Saint-Amand | |
| 4,952,204 A * | 8/1990 | Korteweg | 604/1 |
| 5,084,005 A * | 1/1992 | Kachigian | 604/1 |
| 5,250,412 A * | 10/1993 | Giegel | 435/7.1 |
| 5,266,266 A * | 11/1993 | Nason | 422/58 |
| 5,378,226 A * | 1/1995 | Hanifl et al. | 604/3 |
| 5,611,361 A * | 3/1997 | Leone | 132/218 |
| 5,826,600 A * | 10/1998 | Rowe et al. | 132/317 |
| 6,079,423 A * | 6/2000 | Suzuki | 132/320 |
| 6,357,947 B1 * | 3/2002 | Mark | 401/207 |
| 6,390,708 B1 * | 5/2002 | Gueret | 401/122 |
| 6,406,451 B1 * | 6/2002 | Rowe | 604/1 |
| 6,494,856 B1 | 12/2002 | Zygmont | |
| 6,516,947 B1 * | 2/2003 | Van Dyke et al. | 206/361 |
| 6,811,339 B1 * | 11/2004 | Tsaur | 401/18 |
| 6,957,958 B2 * | 10/2005 | Rowe et al. | 433/89 |

| 7,597,901 B2* | 10/2009 | Clarot et al. | 424/401 |
| 2002/0154935 A1* | 10/2002 | Petrich et al. | 401/126 |
| 2003/0093026 A1* | 5/2003 | Petrich et al. | 604/1 |
| 2003/0173236 A1* | 9/2003 | Van Dyke et al. | 206/210 |
| 2003/0226778 A1* | 12/2003 | Marino | 206/361 |
| 2003/0233063 A1* | 12/2003 | Nakatani | 604/2 |
| 2004/0099543 A1* | 5/2004 | Tsaur | 206/210 |
| 2004/0219107 A1* | 11/2004 | Clarot et al. | 424/45 |
| 2005/0006263 A1* | 1/2005 | Tsaur | 206/368 |
| 2005/0019087 A1* | 1/2005 | Tsaur | 401/132 |
| 2005/0040164 A1* | 2/2005 | Tsaur | 220/4.26 |
| 2005/0123878 A1* | 6/2005 | Lee | 433/80 |
| 2006/0020238 A1* | 1/2006 | Tsaur et al. | 604/2 |
| 2006/0282035 A1* | 12/2006 | Battisti et al. | 604/1 |

FOREIGN PATENT DOCUMENTS

| BR | 8402976 A | 5/1985 |
| CN | 2474117 A | 1/2002 |
| CN | 1352922 A | 6/2002 |
| DE | 9111775 U1 | 2/1992 |
| EP | 0371574 A1 | 6/1990 |
| GB | 2059992 A | 4/1981 |
| GB | 2185880 A | 8/1987 |
| GB | 2371491 A | 7/2002 |
| JP | 55-114644 U | 2/1980 |
| JP | 2-82972 A | 3/1990 |
| JP | 5-503230 A | 6/1993 |
| JP | 6-72876 U1 | 10/1994 |
| JP | 8-666 A | 1/1996 |
| JP | 2000-343879 A | 12/2000 |
| JP | 2001-96970 A | 4/2001 |
| JP | 2003-290317 A | 10/2003 |
| JP | 2003-339767 A | 12/2003 |
| WO | 92/10136 A1 | 6/1992 |
| WO | 9312421 A | 6/1993 |

OTHER PUBLICATIONS

Senese, Fred. "General Chemical Glossary: Paraffin." Accessed Jun. 16, 2012. http://antoine.frostburg.edu/cgi-bin/senese/searchglossary.cgi?query=paraffin&shtml=%2Fchem%2Fsenese%F10%2Fglossary.shtml.*

Merck Index, Fourteenth Edition. "Paraffin." Accessed Jun. 16, 2012. http://themerckindex.cambridgesoft.com/themerckindex/Forms/Search/ContentArea/ChemBioVizSearch.aspx?FormGroupId=200000&AppName=THEMERCKINDEX&AllowFullSearch=true&KeepRecordCountSynchronized=false&CurrentIndex=0&SearchCriteriaId=7&SearchCriteriaValue=2484.*

Online dictionary AskDefine.com "Define thermoplastic." http://thermoplastic.askdefine.com/ accessed Mar. 25, 2013.*

"Injection Molding Handbook" edited by Dominick V. Rosato, Donald V. Rosato, Marlene G. Rosato. Kluwer Academic Publishers. © 2000. pp. 485, 1197, 1200, 1206.*

Supplementary European Search Report dated Apr. 23, 2007, issued in corresponding Application No. EP 04802466.

Notice of Reason for Refusal (JP) dated Apr. 6, 2010, issued in corresponding Japanese Application No. 2006-545888.

* cited by examiner

*Primary Examiner* — Adam Marcetich

(74) *Attorney, Agent, or Firm* — Christensen O'Connor Johnson Kindness PLLC

(57) ABSTRACT

A wiper comprises a rod (20), a wiping body (30) provided at one end of the rod and an outer packing; the rod (20) is of elasticity, the outer packing is a tube-like container (10) having both ends closed permanently and an easy break-off mark (13) provided on the tube wall; the wiper is firm, airtight and capable of being opened easily, and can be used conveniently and rapidly; the rod and the tube-like container are made from thermoplastic materials by technologies such as extruding, injection-molding and the like, both ends of the tube-like container are closed through fusion, mechanical seal and other manners, and the wiper has a simple production technology and is suitable for mass production and wide application.

4 Claims, 8 Drawing Sheets

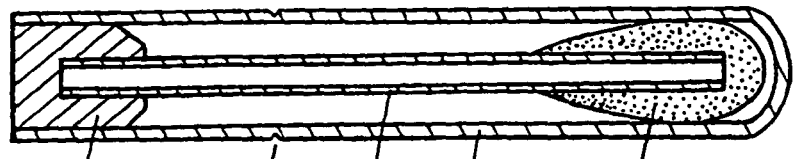
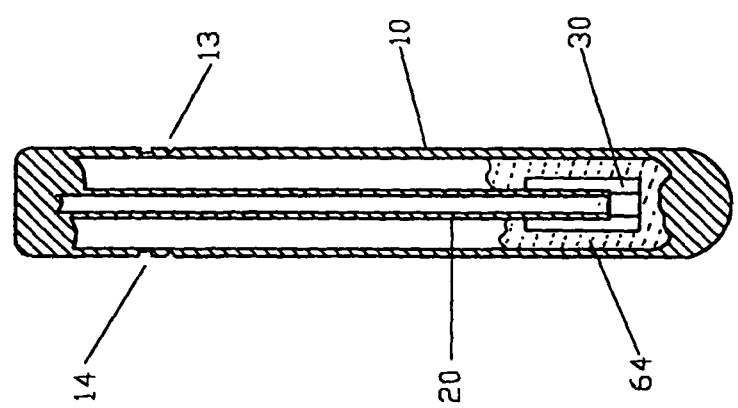
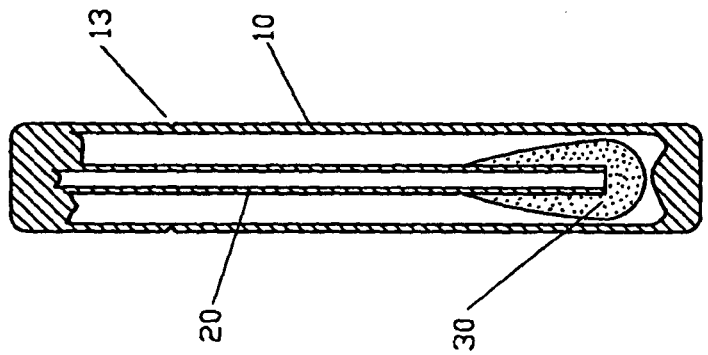
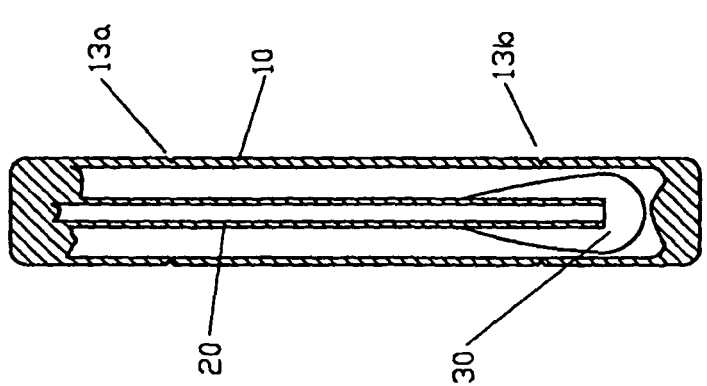

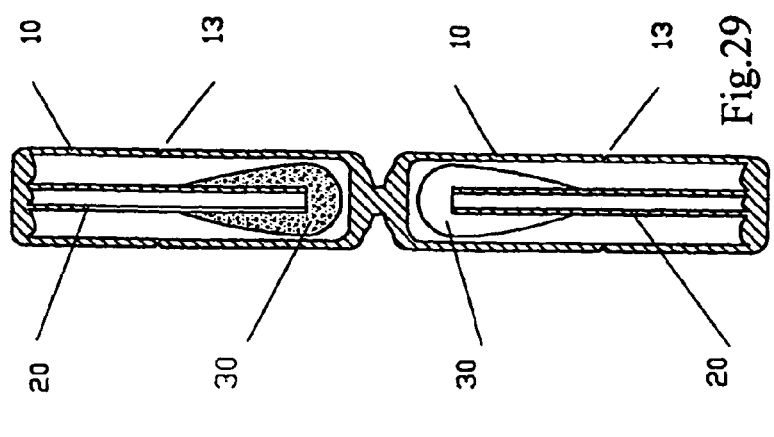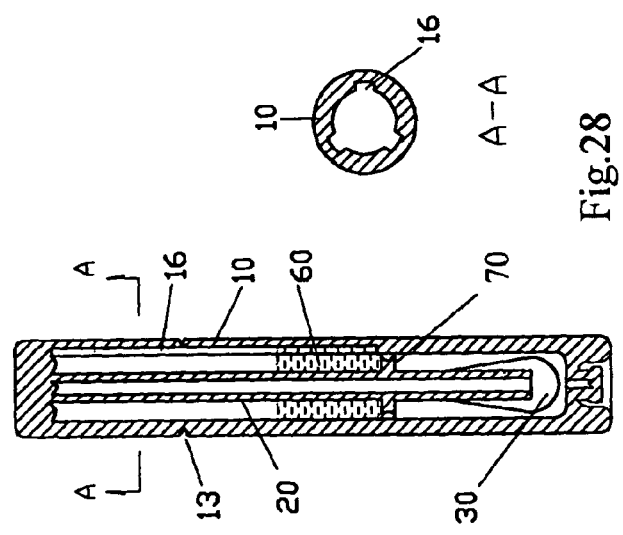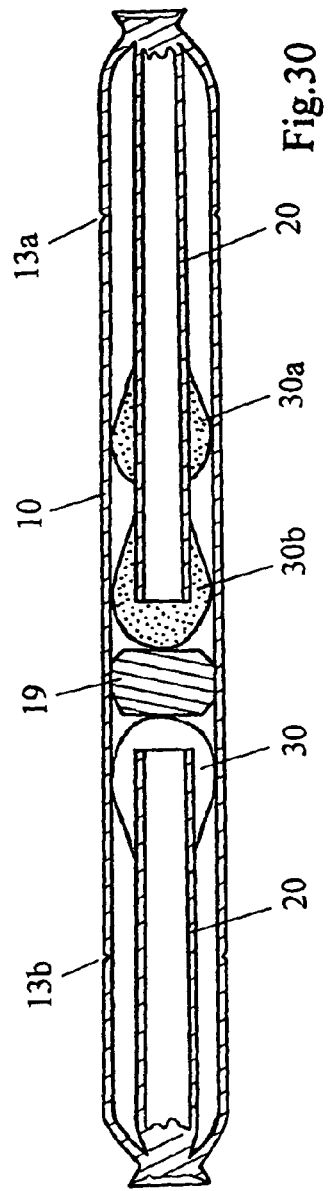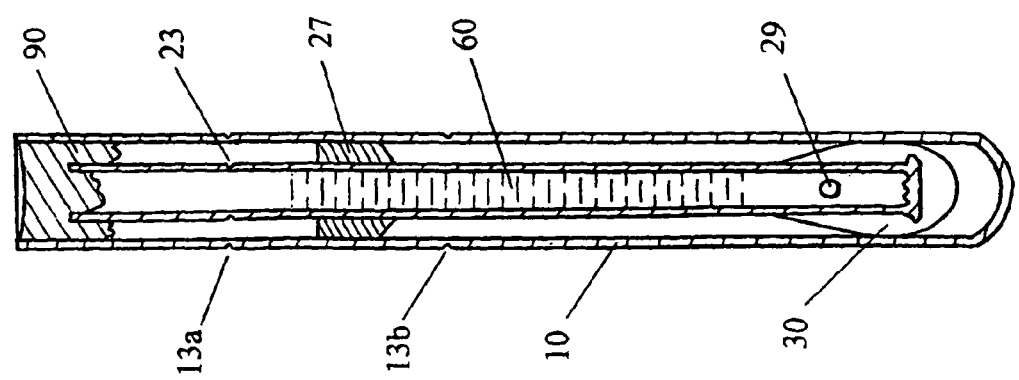

WIPER AND THE PREPARING METHOD THEREOF

BACKGROUND

1. Field of the Invention

The invention relates to a wiping appliance for medical use and daily life use, and particularly, to a wiper and the preparing method thereof.

2. Description of the Prior Art

In medical organizations and in daily life places, wiping appliances have been used more and more widely, in which a wiping body made of soft absorbent material is provided at one end of a rod body. The wiping appliance, such as cotton swabs, is used to wipe away secretions of human body or to sample; after having dipped and impregnated with working fluid such as liquid medicine, disinfectant, and the like, can be used to wipe and sterilize a wound or injection location of human body; also can be used to dip and absorb liquid cosmetic, ointment, powder or other substances for use; further can be used to dip detergent for cleaning; and so on. In recent years, a medicine-containing cotton swab in which a cotton body wound onto one end of a swab rod is impregnated with liquid medicine beforehand, a medicine-containing cotton ball without a rod, and a medicine-containing paper sheet or other products, are used more and more widely; further, a medicine-carrying cotton swab in which working fluid are beforehand filled into a tube-like rod body, and other products have also appeared in succession.

The above products or technical solutions have drawbacks as follows:

Products of cotton swab type have such problems as difficult aseptic manipulation, fragile package, inconvenient use etc. during their use. A conventional cotton swab is packed in a plastic film bag, one end of which needs to be torn away when the same is to be used. However, the cotton swab, when taken out through the torn opening, is readily susceptible to contact with the contaminated torn opening to be bacterium-contaminated, so that the use safety and the sampling accuracy of the cotton swab is disturbed; and during transportation and storage, the cotton swab also would be damaged mechanically due to the infirm plastic film bag or be bacterium-contaminated due to the damage of the bag. In some products or technical solutions, the cotton swab is held in a test-tube-like container with a plug cap closing its tube entrance, and when being used, is taken out after the blocking cap is removed from this tube entrance, such that there is a contradiction that the plug cap should on the one hand seal the tube entrance closely and on the other hand be pulled out easily, thereby the sealing reliability or the use convenience being poor.

The medicine-containing cotton swab has not only problems similar to the cotton swab, but also a problem that the medicine can be volatilized easily. In particular for the medicine-containing cotton swabs packed with a plastic film and an aluminum foil-PVC foam cover, the solution immersed in the cotton body may volatilize and penetrate into the thin foam cover to deteriorate the product.

Also, the technical solution for filling working fluid, such as liquid medicine and the like, into the rod body of the cotton swab has the same problems as those of the medicine-containing cotton swab, i.e. difficult aseptic manipulation, fragile package, inconvenient use etc. Additionally, although the opening end of the rod is blocked with viscous substances such as silicone oil, the volatilization of the medicine cannot be prevented completely, because there are large gaps between the molecules of such viscous substances and thus the molecules of water, alcohol and the like in the working fluid can pass through those gaps easily; the medicine-containing cotton balls, the medicine-containing paper pieces and the like packed with compound film need to be held by clean article upon use, and thus have a disadvantage of requiring strict use environment and manipulation condition; and technical solutions described in some patents not only have a problem of non-tight package and closure, but also have a complex structure, an inconvenient use, and a high manufacture cost. They also have a disadvantage that the production technology requirements of filling the working fluid after sterilization cannot be satisfied, because some working fluid would deteriorate after being sterilized by ethylene oxide, cobalt-60 and the like. During the production of the working fluid-containing cotton swab, cotton ball and paper piece described above, if the cotton swab, cotton ball and paper piece are sterilized after being packed and then the sterilized and sealed package are opened again upon filing the working fluid, it would be contrary to the basic principle of the sterilizing technology.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

An object of the invention is to provide a solid and airtight wiper, which can be opened easily and used almost everywhere safely and regularly, and which facilitates aseptic manipulation and can be used and stored conveniently, and which can be manufactured simply with low cost, and which overcomes the drawbacks described above.

Another object of the invention is to provide a wiper having the advantages of the products described above, which can prevent mis-manipulation and realize aseptic manipulation smoothly and can be used more conveniently and rapidly.

A further object of the invention is to provide a wiper, which not only has the features of sealing, being opened easily and facilitating aseptic manipulation, but also can satisfy the production technology requirements, i.e. firstly sterilizing, secondly filling working fluid.

A further object of the invention is to provide a preparing method of a wiper.

In order to realize the object described above, the technical solutions claimed by the invention are as follows:

A wiper comprises a rod, a wiping body provided at one end of the rod and an outer packing, characterized in that said outer packing is a tube-like container having both ends closed permanently; the tube-like container is provided with an easy break-off mark at least one place between both ends of the tube wall; and the rod is of elasticity.

The invention can be further carried out by following measures:

Said tube-like container is provided with an easy break-off mark at one place near the middle of the tube wall.

Said wiping body comprises one kind of material selected from the group comprising: plant fiber, synthetic fiber, glutin sponge, sponge, soft high molecule absorbent material and brush-like article, and is provided at one end of the rod by one method selected from the group comprising: wounding, wrapping, clamping, shaping and interlinking, binding, and injection-molding integrally with the rod.

Said wiping body is impregnated with fluid.

Said wiping body provided at one end of the rod is divided into two parts along the axial direction of the rod.

Said rod has a cavity containing working fluid, an upper end opening closed through fusion, an easy break-off mark provided at this end portion, and a lower end opening blocked by silicone oil.

Said rod has a cavity containing working fluid, an upper end opening closed by fusion, an easy break-off mark provided at the upper end portion, and a lower end opening closed by a tube-like article, one end of which is connected with an end portion of the tube-like container and sealed, and the other end of which forms interference fit with the lower end opening of the rod.

Inside the tube-like container there is a piston-like article whose diameter corresponds to the inner diameter of the tube-like container, and the tube-like container contains working fluid below the piston-like article, and there are three longitudinal slots arranged equidistantly along the circumference of the inner wall of the tube-like container.

Inside the tube-like container there is a spherical cap-like article, the outer diameter of the upper portion of which corresponds to the inner diameter of the tube-like container and which is deformable when being subjected to a force.

Said tube-like container stores therein at least two rods, with one end of each being provided with a wiping body.

The end of the rod, opposite to the end provided with the wiping body, is fixedly coupled with one end of the tube-like container.

On the wall of said tube-like container between both ends there are provided with easy break-off marks at two places.

In said wiping body there is provided with one substance selected from the group comprising: working fluid, working powder and working ointment.

Said wiping body provided at one end of the rod is divided into two parts along the axial direction of the rod, both being impregnated with working fluid.

Said rod has an easy break-off mark, an upper end connected with a sealing plug which is fused to close the upper end opening of the tube-like container, and a lower end provided with a wiping body, which along the axial direction of the rod is divided into two parts, one of them being impregnated with working fluid.

Said rod has a cavity containing working fluid, an end opening of the end provided with the wiping body closed by a tube-like article, one end of which is connected with an end portion of the tube-like container and sealed, and the other end of which forms interference fit with the lower end opening of the rod, an easy break-off tail tube which extends upwardly from a convex neck provided at the upper portion of the tube-like article being closed at the upper end opening thereof and being provided with an easy break-off mark at the lower portion thereof.

Said rod has a cavity containing working fluid, and an end opening of the end provided with the wiping body being closed by a tube-like article, one end of which is connected with an end portion of the tube-like container and sealed, and the other end of which forms interference fit with the lower end opening of the rod.

Said rod has a cavity containing working fluid, an upper end closed with the upper end opening of the tube-like container through fusion, a middle portion connected with the tube-like container by a connecting member which forms an interference fit with the tube-like container, and an easy break-off mark which is provided on the wall of the rod above the connecting member and corresponds to the easy break-off mark on the outer wall of the tube-like container, and other easy break-off marks may be provided on the outer wall of the tube-like container below the connecting member.

On said rod there is provided with at least one piston-like article, the diameter of which corresponds to the inner diameter of the tube-like container, and above which there are provided with three longitudinal slots arranged equidistantly along the circumference of the inner wall of the tube-like container.

Two wipers are paired up and connected with the tube-like container.

In the middle of the cavity of said tube-like container there is provided with a plug-like article, which divides the cavity into two independent chambers.

The end of said tube-like container is closed permanently by using one method selected from the group comprising: fusion by a heat source, ultrasonic fusion, electromagnetic induction fusion, laser beam fusion, blocking with hot melt adhesive, binding, injection-molding and mechanical sealing.

A preparing method of said wiper comprises the following steps: (1) extruding thermoplastic material into a tubing, cutting the tubing, and scratching an easy break-off mark to form a tube-like container; (2) inserting a rod provided with a wiping body at one end thereof into the tube-like container; and (3) fusing and closing both ends of the tube-like container.

A preparing method of said wiper comprises the following steps: (1) extruding thermoplastic material into a tubing, cutting the tubing, and scratching an easy break-off mark thereon to form a tube-like container; (2) inserting the rod into the tube-like container after the wiping body at one end thereof is impregnated with working fluid; and (3) heat fusing both ends of the tube-like container to close them, with one end of the rod fixedly coupled with one end of the tube-like container through fusion.

A preparing method of said wiper comprises the following steps: (1) injection-molding thermoplastic material into a tube-like container with one end opened and the other end fused and closed, and into a sealing plug, the outer diameter of which corresponds to the inner diameter of the opening end; (2) after inserting an end of the rod opposite to the end provided with the wiping body into a socket pre-arranged inside the sealing plug, inserting the rod into the tube-like container; (3) by using one method selected from the group comprising: ultrasonic wave, electromagnetic induction, bonding and mechanical sealing, the opening end of the tube-like container being fixedly coupled with and closed by the sealing plug; and (4) scratching an easy break-off mark on the wall of the tube-like container.

A preparing method of said wiper comprises the following steps: (1) injection-molding thermoplastic material into a tube-like container with one end opened and the other end fused and closed; (2) scratching an easy break-off mark thereon; (3) filling the tube-like container with working fluid through its opening end; (4) inserting a rod with one end provided with a wiping body into the tube-like container; and (5) by using heating or hot melt adhesive, fusing and closing the opening end of the tube-like container, with one end of the rod being fixedly coupled with said end of the tube-like container through fusion.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

The particular embodiments of the invention are explained below in details in conjunction with accompanying figures, in which:

FIG. 15 shows schematically an axially sectional view of a tenth embodiment of the invention in closed state;

FIGS. 16-22 show schematically axially sectional views of an eleventh embodiment of the invention in closed state;

FIG. 27 shows schematically an axially sectional view of a sixteenth embodiment of the invention in closed state;

FIG. 28 shows schematically an axially sectional view of a seventeenth embodiment of the invention in closed state;

FIG. 29 shows schematically an axially sectional view of an eighteenth embodiment of the invention in closed state; and FIG. 30 shows schematically an axially sectional view of a nineteenth embodiment of the invention in closed state.

Figure 4:
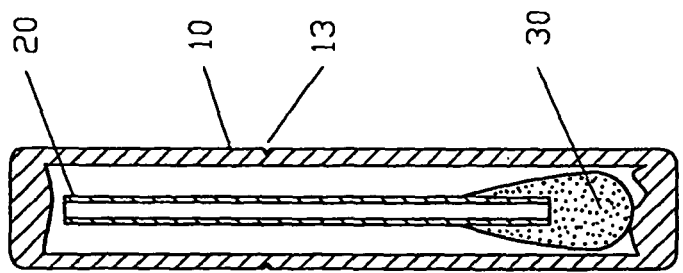
FIG. 4 or FIG. 5 shows schematically an axially sectional view of a second embodiment of the invention in closed state.

The names of various parts indicated by reference numbers in the drawings are:

10 a tube-like container
11 an upper end of the tube-like container
12 a lower end of the tube-like container
13 an easy break-off mark on the tube-like container
14 an indicating mark
15 a technology hole
16 a longitudinal slot
17 a round slot
18 a sealing plug
19 a plug-like article
20 a rod
21 an upper end of the rod
22 a lower end of the rod
23 an easy break-off mark on the rod
24 a tube-like article
25 a convex neck
26 an easy break-off tail tube
27 a connecting member
28 a ring like flange
29 a through hole
30 a wiping body
40 silicone oil
60 working fluid
64 working powder
65 working ointment
70 a piston-like article
71 a spherical cap-like article
72 a rubber plug
80 an electromagnetic induction foil
90 hot melt adhesive

DETAILED DESCRIPTION

Figure 3:
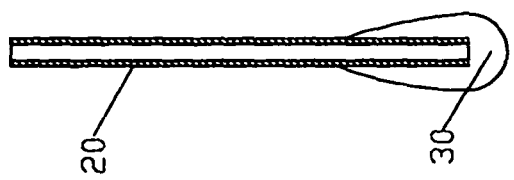
FIG. 3 shows schematically an axially sectional view of the first embodiment of the invention in use.
Figure 2:
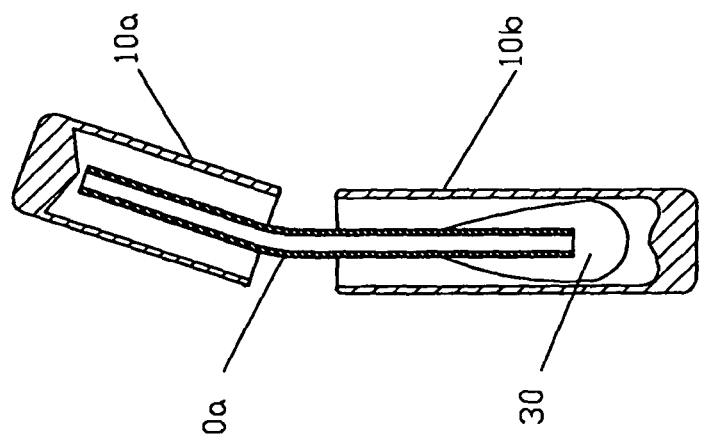
FIG. 2 shows schematically an axially sectional view of the first embodiment of the invention upon broken off.
Figure 1:
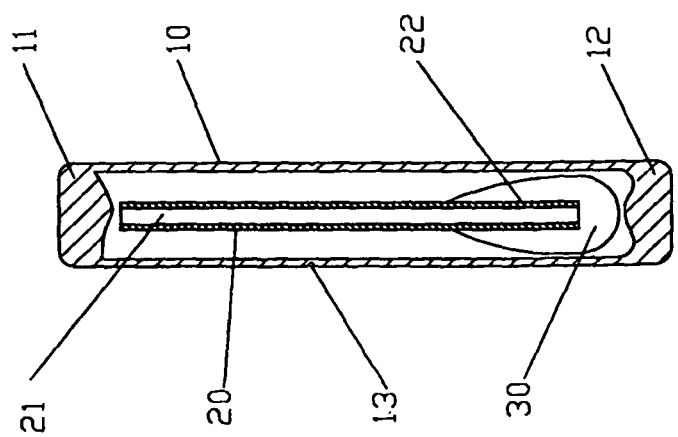
FIG. 1 shows schematically an axially sectional view of a first embodiment of the invention in closed state.

The first embodiment: Referring to FIGS. 1-3, a wiper provided by the invention comprises a rod 20, a wiping body 30 provided at one end of the rod and an outer packing, characterized in that said outer packing is a tube-like container 10 having both ends 11 and 12 closed permanently; the tube-like container 10 is provided with an easy break-off mark 13 at at least one place between both ends of the tube wall; and the rod 20 is of elasticity.

Said tube-like container 10 is provided with an easy break-off mark 13 at one place near the middle of the tube wall between both ends 11 and 12.

Said wiping body 30 comprises one kind of material selected from the group comprising: plant fiber, synthetic fiber, glutin sponge, sponge, soft high molecule absorbent material and brush-like article, and is provided at one end 22 of the rod 20 by one method selected from the group comprising: wounding, wrapping, clamping, shaping and interlinking, binding, and injection-molding integrally with the rod.

Figure 5:
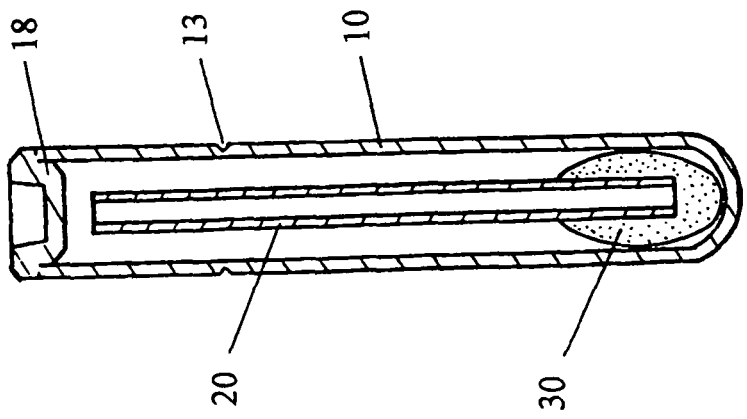

The second embodiment: referring to FIG. 4 or FIG. 5, this embodiment is the same as the first embodiment, except that said wiping body 30 is impregnated with working fluid.

Figure 6:
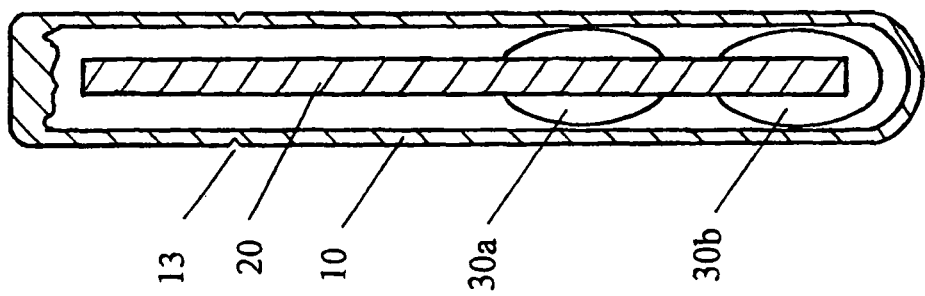
FIG. 6 shows schematically an axially sectional view of a third embodiment of the invention in closed state.

The third embodiment: referring to FIG. 6, this embodiment is the same as the first embodiment, except that said wiping body 30 provided at one end of the rod 20 is divided into two parts 30a and 30b along the axial direction of the rod.

Figure 7:
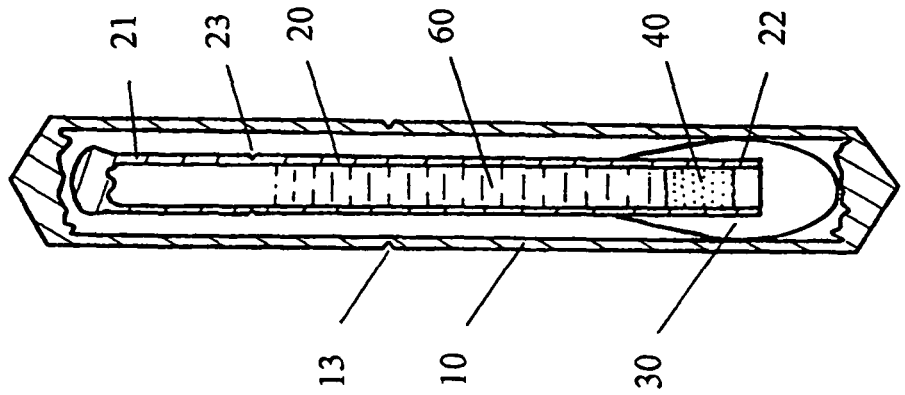
FIG. 7 shows schematically an axially sectional view of a fourth embodiment of the invention in closed state.

The fourth embodiment: referring to FIG. 7, this embodiment is the same as the first embodiment, except that said rod 20 has a cavity containing working fluid 60, an upper end opening 21 closed by fusion, an easy break-off mark 23 provided at this end portion, and a lower end opening 22 blocked by silicone oil 40.

Figure 8:
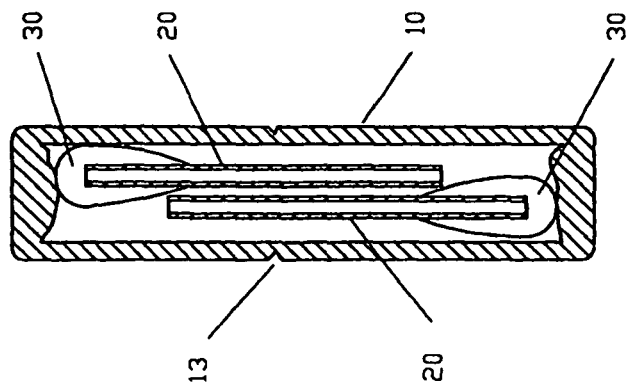
FIG. 8 shows schematically an axially sectional view of a fifth embodiment of the invention in closed state.

The fifth embodiment: referring to FIG. 8, this embodiment is the same as the first embodiment, except that said rod 20 has a cavity containing working fluid 60, an upper end opening closed by fusion, an easy break-off mark 23 provided at this end portion, and a lower end opening 22 closed by a tube-like article 24, which is connected with an end portion of the tube-like container and one end of which is sealed.

The sixth embodiment: referring to FIG. 9, this embodiment is the same as the first embodiment, except that inside the tube-like container 10 there is a piston 70 whose diameter corresponds to the inner diameter of the container 10, and the container 10 contains working fluid 60 below the piston 70, and on the inner wall of the tube-like container there are provided with three longitudinal slots 16 arranged equidistantly along the circumference.

Figure 10:
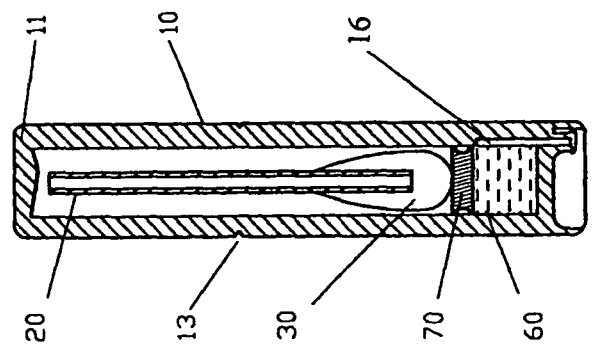
FIG. 10 shows schematically an axially sectional view a seventh embodiment of the invention in closed state.

The seventh embodiment: referring to FIG. 10, this embodiment is the same as the first embodiment, except that inside the tube-like container 10 there is a spherical cap-like article 71, the outer diameter of the upper portion of which corresponds to the inner diameter of the tube-like container 10 and which is deformable when being subjected to a force.

Figure 11:
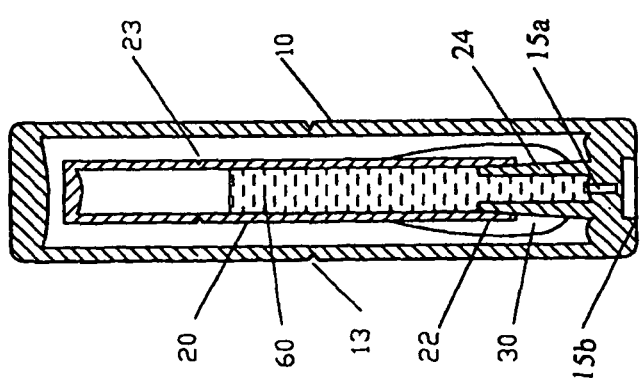
FIG. 11 shows schematically an axially sectional view of an eighth embodiment of the invention in closed state.

The eighth embodiment: referring to FIG. 11, this embodiment is the same as the first embodiment, except that said tube-like container 10 stores therein at least two rods 20, with one end of each being provided with a wiping body 30.

Figure 14:
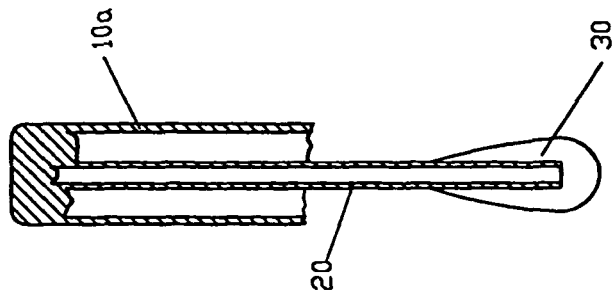
FIG. 14 shows schematically an axially sectional view the ninth embodiment of the invention in use.
Figure 13:
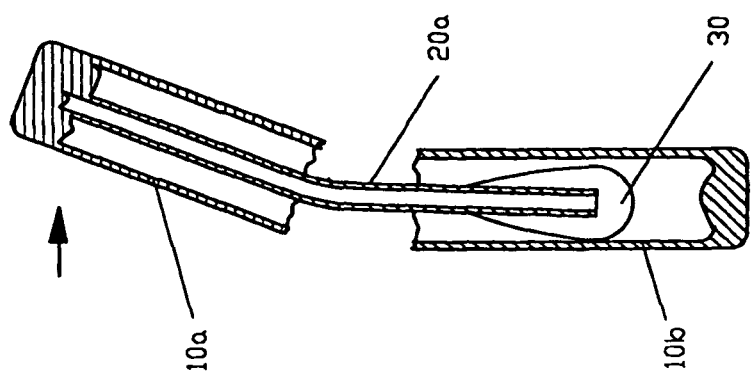
FIG. 13 shows schematically an axially sectional view of the ninth embodiment of the invention upon broken-off.
Figure 12:
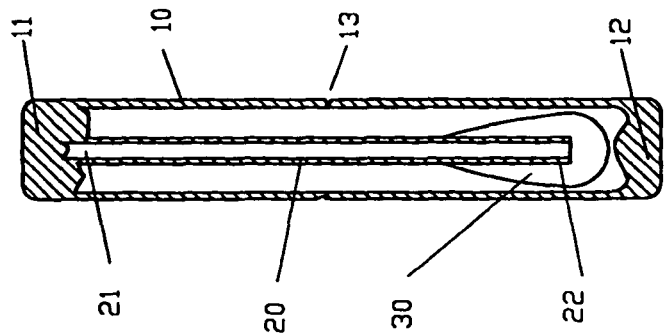
FIG. 12 shows schematically an axially sectional view of a ninth embodiment of the invention in closed state.

The ninth embodiment: referring to FIGS. 12-14, this embodiment is the same as the first embodiment, except that end 21 of the rod 20, opposite to the end provided with the wiping body 30, is fixedly coupled with end 11 of the tube-like container 10.

The tenth embodiment: referring to FIG. 15, this embodiment is the same as the first or ninth embodiment, except that on the wall of said tube-like container 10 between both ends there are provided with easy break-off marks 13a and 13b at two places.

The eleventh embodiment: referring to FIGS. 16-22, this embodiment is the same as the first or ninth embodiment, except that in said wiping body 30 there is provided with one substance selected from the group comprising: working fluid 60, working powder 64 and working ointment 65.

Figure 23:
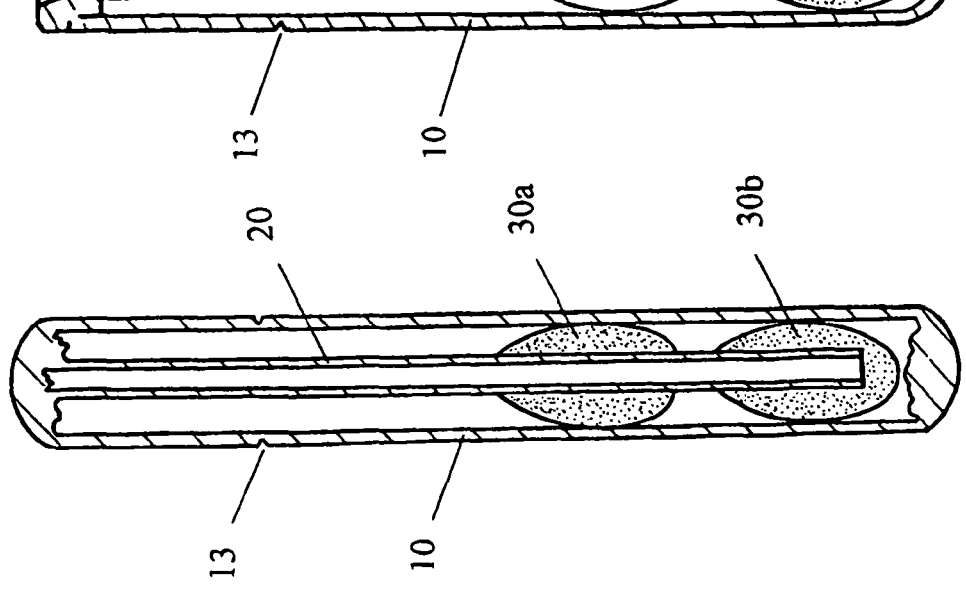
FIG. 23 shows schematically an axially sectional view of a twelfth embodiment of the invention in closed state.

The twelfth embodiment: referring to FIG. 23, this embodiment is the same as the first or ninth embodiment, except that said wiping body 30 provided at one end of the rod 20 is divided into two parts 30a and 30b along the axial direction of the rod, both being impregnated with working fluid.

Figure 24:
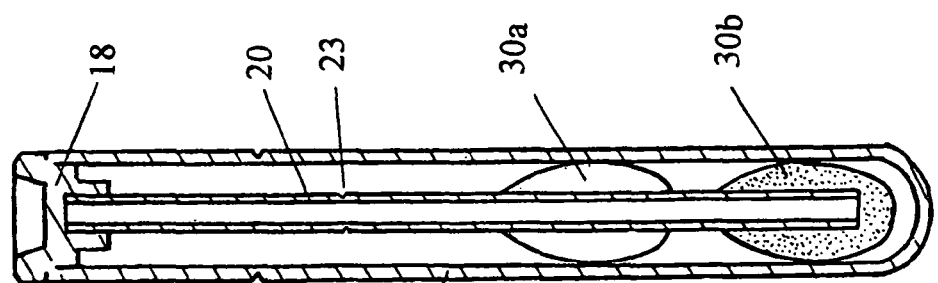
FIG. 24 shows schematically an axially sectional view of a thirteenth embodiment of the invention in closed state.

The thirteenth embodiment: referring to FIG. 24, this embodiment is the same as the first or ninth embodiment, except that said rod 20 has an easy break-off mark 23, an upper end connected with a sealing plug 18 which closes the upper end opening of the tube-like container 10 through fusion, and a lower end provided with a wiping body 30, which along the axial direction of the rod is divided into two parts 30a and 30b, part 30b being impregnated with working fluid.

Figure 25:
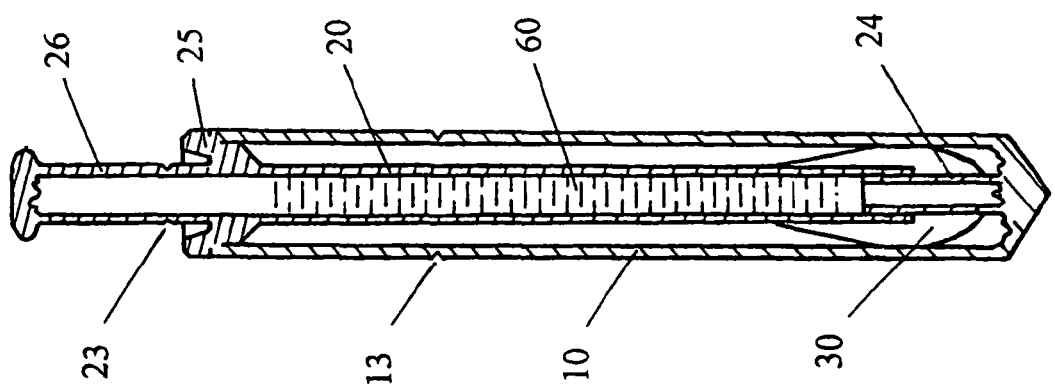
FIG. 25 shows schematically an axially sectional view of a fourteenth embodiment of the invention in closed state.

The fourteenth embodiment: referring to FIG. 25, this embodiment is the same as the first or ninth embodiment, except that said rod 20 has a cavity containing working fluid 60, an end opening of the end provided with a wiping body 30 closed by a tube-like article 24 which is connected with an end portion of the tube-like container 10 and one end of which is sealed, a convex neck 25 provided at the upper portion and closing the upper end opening of the tube-like container 10 through fusion, and an easy break-off tail tube 26 which extends upwardly from the convex neck, its upper end opening being closed and its lower portion being provided with an easy break-off mark 23.

Figure 26:
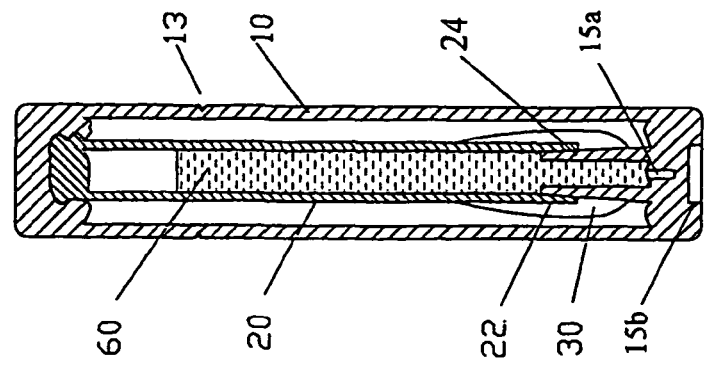
FIG. 26 shows schematically an axially sectional view of a fifteenth embodiment of the invention in closed state.

The fifteenth embodiment: referring to FIG. 26, this embodiment is the same as the first or ninth embodiment, except that said rod 20 has a cavity containing working fluid 60, and an end opening of the end 22 provided with wiping body 30 closed by a tube-like article 24, which is connected with an end portion of the tube-like container and one end of which is sealed.

The sixteenth embodiment: referring to FIG. 27, this embodiment is the same as the first or ninth embodiment, except that said rod 20 has a cavity containing working fluid 60, an upper end closed with the upper end opening of the tube-like container 10 through fusion, a middle portion connected with the tube-like container by a connecting member 27 which forms interference fit with the tube-like container, and an easy break-off mark 23 which is on the tube wall above the connecting member and corresponds to the easy break-off mark 13a on the outer wall of the tube-like container.

The seventeenth embodiment: referring to FIG. 28, this embodiment is the same as the first or ninth embodiment, except that on said rod 20 there is provided with at least one piston-like article 70, the diameter of which corresponds to the inner diameter of the tube-like container 10 and above which there are provided with three longitudinal slots 16 arranged equidistantly along the circumference of the inner wall of the tube-like container.

The eighteenth embodiment: referring to FIG. 29, this embodiment is the same as the first or ninth embodiment, except that two wipers are paired up and connected with each other.

The nineteenth embodiment: referring to FIG. 30, this embodiment is the same as the first or ninth embodiment, except that in the middle of the cavity of said tube-like container 10 there is provided with a plug-like article 19, which divides the cavity into two independent chambers.

The first preparing method: the ends of said tube-like container are closed permanently by using one of the following means: heat fusion with heat source, ultrasonic fusion, electromagnetic induction fusion, laser beam fusion, blocking with hot melt adhesive, binding, injection-molding and mechanical sealing.

The second preparing method: a preparing method of said wiper comprises the following steps: (1) extruding thermoplastic material into a tubing, cutting the tubing, and scratching an easy break-off mark thereon to form a tube-like container; (2) inserting a rod provided with a wiping body at one end thereof into the tube-like container; and (3) fusing and closing both ends of the tube-like container.

The third preparing method: a preparing method of said wiper comprises the following steps: (1) extruding a thermoplastic material into a tubing, cutting the tubing, and scratching an easy break-off mark to form a tube-like container; (2) inserting the rod provided with a wiping body at one end thereof into the tube-like container after the wiping body is impregnated with working fluid; and (3) heat fusing both ends of the tube-like container to close them, with one end of the rod fixedly coupled with one end of the tube-like container through fusion.

The fourth preparing method: a preparing method of said wiper comprises the following steps: (1) injection-molding thermoplastic material into a tube-like container with one end opened and the other end fused and closed, and into a sealing plug, the outer diameter of which corresponds to the inner diameter of the opening end; (2) after inserting the end of the rod opposite to the end provided with a wiping body into a socket pre-arranged inside the sealing plug, inserting the rod into the tube-like container; (3) by using one method selected from the group comprising: ultrasonic wave, electromagnetic induction, bonding and mechanical sealing, the opening end of the tube-like container being fixedly coupled with and closed by the sealing plug; and (4) scratching an easy break-off mark on the wall of the tube-like container.

The fifth preparing method: a preparing method of said wiper comprises the following steps: (1) injection-molding thermoplastic material into a tube-like container with one end opened and the other end fused and closed; (2) scratching an easy break-off mark; (3) filling the tube-like container with working fluid through its opening end; (4) inserting a rod with one end provided with a wiping body into the tube-like container; and (5) by using heating or hot melt adhesive, fusing and closing the opening end of the tube-like container, with one end of the rod being fixedly coupled with this end of the tube-like container through fusion.

Technical Results of the Invention

The invention makes full use of the characteristics of thermoplastic material, and delicately combines the structure, function, use and package of the product to make it become a novel product which is firm, airtight and capable of being opened easily, has a simple structure, and can be used conveniently. The invention advantageously integrates the function of the outer packing into the product itself, thus greatly improving the use performance of the product. The tube-like container having both ends sealed permanently is completely different from the conventional concept of bag type package, and comparing with a film packing bag, not only is firm, but also uses the principle of stress concentration, i.e. providing an easy break-off mark on the tube wall of the tube-like container, to open the tube-like container, so that the product can be opened and used quite conveniently; the characteristics that the rod can be deformed elastically allow the tube-like container being broken off easily along the pre-arranged easy break-off mark and allow the rod resuming its original shape and function; the solution for fixedly coupling one end of the rod to one end of the tube-like container completely eliminates mis-manipulation during the use of the product, and greatly improves the use convenience and rapidity of the product; the design that the tube-like container is broken off at its middle portion and the wiping body is taken out from the broken-off opening at this middle portion, especially has a feature which not only allows the product to be used conveniently and rapidly but also brings about the following prominent advantages: firstly, both ends of the tube-like container may be closed permanently to form a integral unit by using the technology such as fusion seal, mechanical seal and the like, and the wiping body, the rod as well as the working fluid etc. provided in the container are sealed tightly and thus can be stored safely for a long time, thereby overcoming the disadvantages, such as complex seal structure, unstable effects, inconvenient unclosing etc. in the conventional technical solutions, in which the end opening of the tube-like container is not permanently closed, that is, the end opening is closed by a seal member which may be pulled out upon use, whereas closing permanently in the present invention means that it is unnecessary or impossible to open the closed end openings of the tube-like container through a conventional method; secondly, taking out the wiping body from near the middle broken-off opening may assure aseptic manipulation effectively during use.

Referring to FIGS. 1-3 of the first embodiment, the wiping body 30 which optionally comprises a cotton plant fiber is connected to the lower end of the rod by wounding to form a conventional cotton swab. The cotton swab is placed into the tube-like container 10, both ends 11 and 12 of which are sealed by fusion. Thus, as shown in FIG. 1, the cotton swab provided in the tube-like container may be sealed completely and stored aseptically for a long time after being sterilized; upon use, both hands respectively grasp the two ends of the tube-like container 10 and bend it slightly by force, as shown in FIG. 2, the tube-like container 10 is broken off along the pre-arranged easy break-off mark 13 into two parts 10a and 10b, and the rod 20 having elasticity is deformed into a shape 20a under force and thus does not interfere with the breaking-off of the tube-like container 10, and since the upper end of the rod is higher than the cross section of the tube-like container having the easy break-off mark 13, the upper end of the rod is exposed out of the broken opening of the broken end 10b; the cotton swab is taken out as shown in FIG. 3 and can be used to wipe directly. In the whole process, both hands do not touch the end surface of near the middle broken opening of the tube-like container and the pulled-out cotton body, so that contamination is prevented.

Referring to FIG. 4 or FIG. 5 of the second embodiment, the wiping body such as cotton is impregnated with working fluid such as liquid medicine in advance, and after being exposed by breaking-off and unclosing, the wiping body 30 with liquid medicine can be used to wipe immediately.

Referring to FIG. 6 of the third embodiment, the wiping body 30 is divided into two parts. Upon use, part 30a is used to wipe for the first time and part 30b is used to wipe for the second time, thereby advantageously satisfying the use requirements of wiping for two times. According to requirements, the wiping body may also be divided into three or more parts. The rod 20 can employ natural material such as a bamboo rod, a wood rod and the like having good elasticity, or can use other suitable material.

Referring to FIG. 7 of the fourth embodiment, working fluid 60 dose not contact with the wiping body 30, so as to solve the problem that the wiping body 30 is not suitable for immersing into certain working fluid 60 for a long time. When in use, the tube-like container 10 is broken off and opened along the easy break-off mark 13 thereon, and then the upper end of the rod is broken off along the easy break-off mark 23 thereon, so that the upper end of the cavity of the rod is open to atmosphere, and the working fluid 60 passes through the silicone oil 40 by gravity, to flow out and wet down the wiping body 30, thereby using it immediately after being taken out. Before use, since the tube-like container 10 has good airtightness, the volatile molecules of the working fluid escapes through the silicone oil until a saturation pressure is reached in the closed cavity of the tube-like container, and therefore, the working fluid can be stored stably before use.

Referring to FIG. 8 of the fifth embodiment, this embodiment differs from the fourth embodiment in that: a tube-like article 24 is inserted into the lower end opening of the rod 20 which contains working fluid 60 inside the cavity, and an interference fit is formed therebetween so that the lower end opening is closed. Upon use, the rod 20 is drawn upwards and is separated from the tube-like article 24 since the lower end of the tube-like article 24 is connected with the lower end of the tube-like container 10.

Therefore, the lower end opening of the rod is opened and working fluid 60 flows out of the lower end opening to wet the wiping body 30, so the wiping body 30 can be used immediately after being taken out. Technology holes 15a and 15b are shown in FIG. 8. This embodiment is very applicable to a case in which working fluid 60 is not suitable for contacting with viscous oil substances such as silicone oil.

Figure 9:
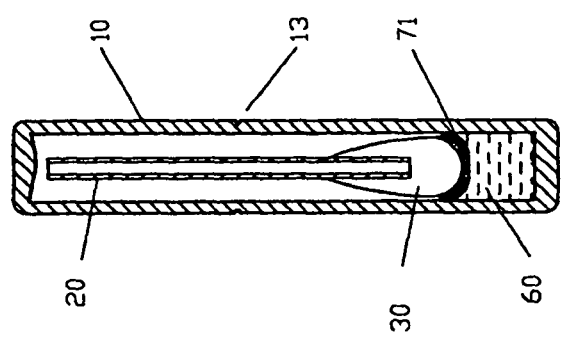
FIG. 9 shows schematically an axially sectional view of a sixth embodiment of the invention in closed state.

Referring to FIG. 9 of the sixth embodiment, inside the tube-like container 10 there is a piston-like article 70 which corresponds to the inner diameter of the cavity and separates the working fluid 60 from the wiping body 30. When in use, the tube-like container 10 is broken off, and the rod is pressed downward by grasping its end, so that the piston-like article 70 is displaced downward along the inner wall of the tube-like container, and the working fluid 60 flows out from longitudinal slots 16 under pressure to wet the wiping body 30.

Referring to FIG. 10 of the seventh embodiment, for the product provided by this technical solution, when in use, the rod is pressed downwards by grasping its end, so that the spherical cap-like article 71 having elasticity would, due to its deformation while being displaced downwards by force, create a gap with the tube wall, allowing the working fluid 60 to flow out through the gap and wet down the wiping body 30.

Referring to FIG. 11 of the eighth embodiment, said tube-like container 10 stores therein at least two rods 20, with one end of each being provided with one wiping body 30, and after the tube-like container 10 is broken off at its middle portion, each of the broken parts has one wiping body 30; and the tube-like container also can store therein a plurality of wiping bodies 30.

Referring to FIGS. 12-14 of the ninth embodiment, the wiping body 30 which optionally comprises for example cotton plant fiber is connected to the lower end of the rod by wounding to form a conventional cotton swab. This cotton swab is placed into the tube-like container 10, and the rod end 21 and tube-like container end 11 are fused concurrently. While the upper end of the tube-like container 10 is being sealed, the upper end 21 of the rod 20 is fixedly coupled with the upper end 11 of the tube-like container 10. Therefore, as shown in FIG. 12, the cotton swab provided in the tube-like container is sealed and can be stored aseptically for a long time after being sterilized; upon use, both hands respectively grasp the two ends of the tube-like container 10 and bend it slightly, as shown in FIG. 13, the tube-like container 10 is broken off along the pre-arranged easy break-off mark 13 into two parts 10a and 10b, and the rod 20 having elasticity is deformed into an elastic shape 20a under force and thus does not interfere with the breaking-off of the tube-like container 10; as shown in FIG. 14, since the upper end of the rod 20 has been fixedly coupled to the upper end of the tube-like container, the hand grasping the upper part 10a of the tube-like container need not move and the lower end 10b can be removed conveniently by the other hand grasping it, then the wiping body 30 is exposed to be directly used for wiping. This solution allows the product and its package into an integral unit, and since not only the product itself is firm and airtight, and can be opened conveniently, but also both hands have no repeated or undesired actions, both hands never touch the end surfaces of the broken opening of the tube-like container and the wiping body taken out from this broken opening to cause contamination, thus the mis-manipulation in use are prevented and the use speed of the product is improved greatly. When in use, since part 10a of the tube-like container is much thicker than the rod of the cotton swab, the grasping is more convenient so as to facilitate the rotation of the cotton body and the wiping.

Referring to FIG. 15 of the tenth embodiment, the product provided by this technical solution has two easy break-off marks 13a and 13b at two places symmetric with respect to the middle of the tube-like container 10, to allow the process for selecting the direction of the easy break-off mark during production to be omitted, so that the productivity is increased. The rod 20 can also use natural material such as a bamboo rod, a wood rod and the like having good elasticity, and the upper end of the rod can be embedded into the fused and closed upper end of the tube-like container to be fixedly coupled thereto.

Figure 20:
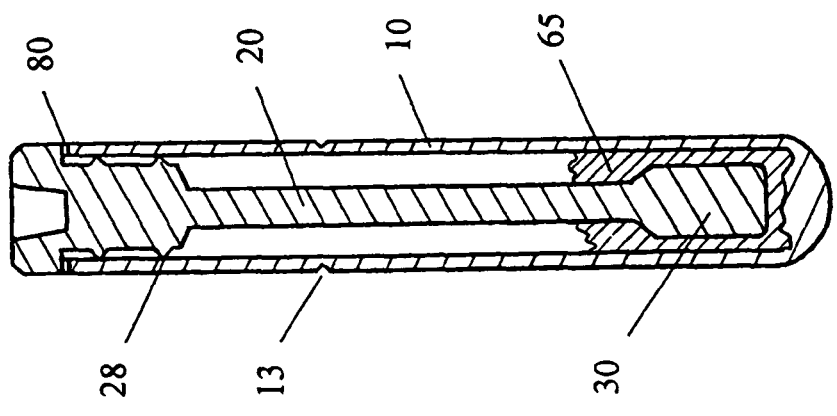
Figure 19:
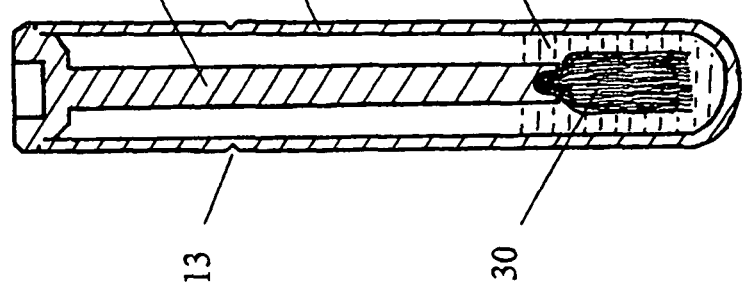

Referring to FIG. 16, FIG. 18, FIG. 21 and FIG. 22 of the eleventh embodiment, the wiping body such as cotton is impregnated with working fluid 60 such as liquid medicine in advance, and after being exposed due to break off and open, the wiping body 30 being impregnated with liquid medicine can be used to wipe the treated location directly; referring to FIG. 17, the wiping body 30 is a kind of soft high molecule absorbent material, and after being shaped (presenting a hollow cylindrical shape), is interlinked with the lower end of the rod and placed into working powder 64, and an indicating mark 14 is provided near the easy break-off mark 13 at the upper portion of the tube-like container, so that in the case the tube-like container 10 is opaque, the end of the tube-like container 10 in which there is no wiping body 30 is grasped accurately by right hand or left hand according to use habit; referring to FIG. 19, the wiping body 30 is a brush-like article which is held onto the lower end of the rod and immersed into working fluid 60 which can be detergent, glue and the like; referring to FIG. 20, the wiping body 30 is a brush-like article of flat plate type which is inserted into the working ointment 65, injection-molded integrally with the rod 20 and provided at one end of the rod. The brush-like article of flat plate type can also be provided thereon with several small through-holes, so as to dip working fluid for wiping. Thus, different wiping use requirements can be satisfied and the use is more convenient.

Referring to FIG. 23 of the twelfth embodiment, the wiping body 30 provided at one end of the rod 20 is divided along the axial direction of the rod into two parts 30a and 30b, both being impregnated with working fluid such as disinfectant, and upon use, part 30b is used to wipe and sterilize for the first time and part 30a is used to wipe and sterilize for the second time, thereby satisfying the use requirements, i.e. wiping two times for sterilization treatment; parts 30a and 30b may absorb the same working fluid, or different kinds of working fluid which preferably have the same or similar solvents.

Referring to FIG. 24 of the thirteenth embodiment, it can satisfy the use requirements that working fluid is removed by wiping after being applied. For example, part 30b with liquid medicine is used to wipe a small wound, subsequently the surplus liquid medicine around the wound is removed by using part 30a, and then the wound is covered with a bandage or other covering materials in order to protect the wound. Having been used, the rod 20 can be broken off along the easy break-off mark 23 provided thereon and the end with the wiping body is thrown away, so that most material can be recovered to reuse and the contaminated waste is reduced significantly, thus realizing environment protection; if necessary, other technical solutions of the invention can use similar measures for environment protection purpose.

Referring to FIG. 25 of the fourteenth embodiment, this technical solution not only allows working fluid 60 not contacting with the wiping body 30 before use, but also more importantly satisfies the production technology requirements, i.e. sterilizing at first, then filling the working fluid. The lower end opening of the rod 20 forms an interference fit with the tube-like article 24, which has a lower end free of cotton body 30 and connected with the lower end of the tube-like container through fusion; the convex neck 25 provided at the upper portion of rod closes the upper end opening of the tube-like container 10 through fusion by means of ultrasonic technology. After being subjected to sterilization treatment, the chamber containing the cotton body 30 is in aseptic state, and working fluid 60 is filled into the cavity of the rod 20 through the upper end opening of the easy break-off tail tube 26 which extends upwards from the upper convex neck 25 of the rod, and then the upper end opening of the easy break-off tail tube 26 is closed by fusion. Upon use, the easy break-off tail tube 26 is broken off along the easy break-off mark 23, and the tube-like container 10 is broken off along the easy break-off mark 13, then the upper end of the tube-like container 10 is pulled upwards, so that the air-tight interference fit between the lower end opening of the rod 20 and the tube-like article 24 is broken, and working fluid 60 flows out of the lower end opening of the rod 20 to wet down the cotton body 30, which can be used immediately after being taken out. If necessary, said easy break-off tail tube 26 can be covered with an ornament cap or a protect case.

Referring to FIG. 26 of the fifteenth embodiment, it is the same as the fourteenth embodiment except that the upper end of the rod 20 with its cavity containing working fluid 60 is connected with the upper end of the tube-like container 10, and need not be broken off to communicate with atmosphere upon use as long as the tube-like container 10 is broken off along the easy break-off mark 13 and the upper broken part is pulled upwards, and if the diameter of the cavity of the rod 20 is greater than 3.5 mm, the working fluid 60 would flow out of the lower end opening of the rod 20 to wet down the cotton body 30; if the inner diameter of the rod 20 is small or the working fluid is viscous and thick, the upper part of the tube-like container broken along the easy break-off mark 13 can be swung slightly, so that the working fluid 60 would be swung out of the lower end opening of the rod 20 to wet down the cotton body 30. Reference numerals 15a and 15b represent respectively the technology holes for production. This technical solution is especially suitable for the products which need relative large amount of working fluid, and can also satisfy the production technology requirements, i.e. firstly sterilizing, then filling working fluid. If necessary, longitudinal slots may be provided on the inner wall of the cavity of the rod 10, to facilitate working fluid 60 in the cavity of the rod to flow out rapidly.

Referring to FIG. 27 of the sixteenth embodiment, the easy break-off mark 13a at the upper portion of the tube-like container 10 and the easy break-off mark 23 at the upper portion of the rod 20 are about on the same level, and upon use the tube-like container 10 and the rod 20 can be broken off and opened simultaneously. Therefore, working fluid 60 in the cavity of the rod 20 would flow out of its lower through hole 29 to wet down the cotton body 30, and after that the tube-like container 10 is broken off along the easy break-off mark 13b thereon and the cotton body 30 is taken out for use.

Referring to FIG. 28 of the seventeenth embodiment, for the product provided by this technical solution, the tube-like container 10 is broken off along the easy break-off mark 13, and the piston-like article 70 is displaced upwards in the tube-like container 10, and when it reaches the longitudinal slots 16 on the inner wall of the tube-like container 10, the working fluid 60 will leak downward through the longitudinal slots 16 to wet down the cotton body 30. In order to prevent working fluid 60 from splashing out of the upper portion due to possible mis-manipulation, another piston-like article can be provided at a proper position above the piston-like article 70. The tube-like container 10 and the rod with the piston-like article 70 can be made by injection-molding.

Referring to FIG. 29 of the eighteenth embodiment, two wipers are connected with each other either axially or side by side. The wiping bodies can be selected as follows: neither contains working substances such as medicine; one does not contain medicine, but the other contains medicine; or both contain medicine, for example, one contains liquid medicine for cleaning and sterilizing a wound and the other contains certain biological glue for protecting the wound, thus, one can be used to clean and sterilize the wound and the biological glue of the other is applied to the wound for protecting. Different market requirements therefore can be satisfied.

Referring to FIG. 30 of the nineteenth embodiment, a plug-like article 19 is arranged in the middle of the cavity of the tube-like container 10 and divides the cavity into two independent chambers, one containing two wiping bodies with working fluid, and the other containing one wiping body, thus realizing the purpose that one tube has double uses.

Figure 22:
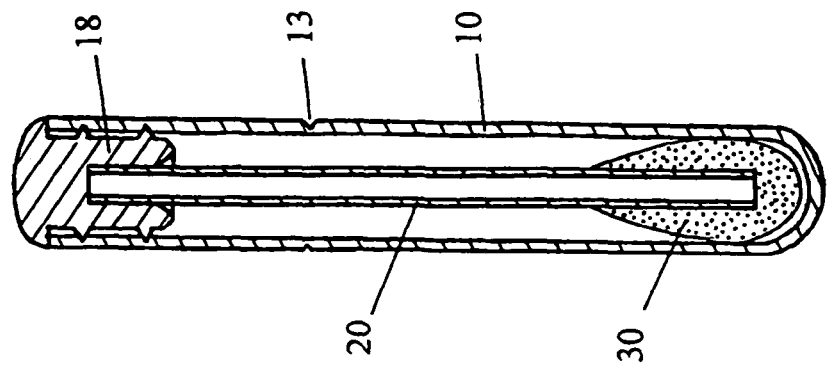
Figure 21:
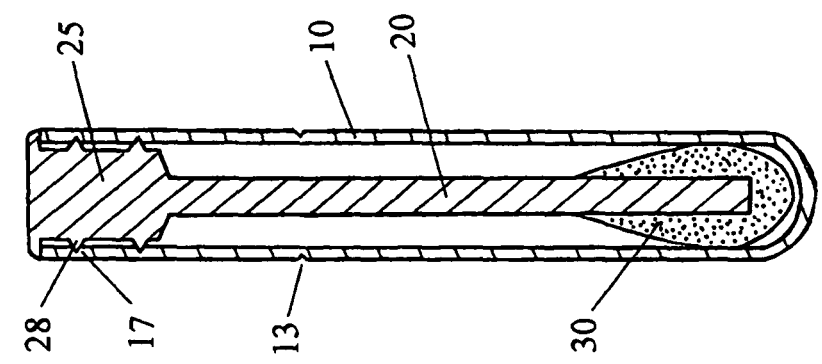

Referring to the first preparing method, according to the structure characteristics, the sequence of the process, the production cost etc., both ends of the tube-like container of the invention are closed by using simultaneously or respectively heating, ultrasonic wave, electromagnetic induction, injection-molding, hot melt adhesive, binding, mechanical sealing, and other technologies, which are all common known industrial techniques. As in the first embodiment (see FIG. 1), the twelfth embodiment (see FIG. 23), and the nineteenth embodiment (see FIG. 30), both ends of the tube-like container are closed through heat fusing with heat source, and both ends of the tube-like container shown in FIG. 30 are fused by heating with heat source and kneaded; as in the third embodiment (see FIG. 6) and the sixth embodiment (see FIG. 9), the lower end of the tube-like container is closed through fusion during the injection-molding thereof, and its upper end is closed through fusion with heat source; further as in the second embodiment (see FIG. 5) and the thirteen embodiment (see FIG. 24), the lower end of the tube-like container is closed through fusion during the injection-molding thereof, and its upper end is fused and closed by using ultrasonic means; further as in the eleventh embodiment (see FIG. 20), the upper end of the rod and the upper end of the tube-like container form a mechanical seal in advance, and then the upper end surface of the tube-like container is fused and closed with heat produced by the electromagnetic induction foil 80 by using electromagnetic induction technology; further as in the sixteenth embodiment (see FIG. 27), the upper end of the rod and the upper end of the tube-like container are connected and closed by using hot melt adhesive; further as in the eleventh embodiment (see FIG. 19), the upper end of the rod and the upper end of the tube-like container are fixedly coupled together and closed by using adhesive. Further as in the eleventh embodiment (see FIG. 18, FIG. 21 and FIG. 22), the upper end of the tube-like container adopts mechanical seal, as shown in FIG. 18, the upper end opening of the tube-like container 10 is closed by a rubber plug 72, the upper end of the rod 20 is inserted into a connection hole at the lower portion of the rubber plug 72 so as to be fixedly coupled with the end of the tube-like container 10, and since the rubber plug 72 sinks into the upper end opening of the tube-like container 10 and can not be pulled out, the upper end is closed permanently; as shown in FIG. 21, the upper end opening of the tube-like container 10 is closed by inserting the convex neck 25 which is injection-molded integrally with the rod 20 and has a cylindrical shape, and two round flanges 28 provided on the convex neck 25 correspond to and form an interference fit with two round slots 17 provided on the inner wall of the upper end of the tube-like container 10, so that the opening end of the tube-like container 10 is closed permanently; and as shown in FIG. 22, the upper end opening of the tube-like container 10 is closed by the sealing plug 18, and its mechanical seal manner is similar to that shown in FIG. 21. Other commonly known mechanical seal manners also can be selected to close the end opening of the tube-like container. The means of fixedly coupling the upper end of the rod with the upper end portion of the tube-like container described in the invention are as follows: integral fusion connection as shown in the ninth embodiment (see FIG. 12); the upper end of rod being inserted into the seal member fixedly coupled to the upper opening end of the tube-like container, as shown in FIG. 18 and FIG. 22 of the eleventh embodiment; and injection-molding integrally with the seal member inserted into the upper opening end of the tube-like container, as shown in FIG. 19 and FIG. 21 of the eleventh embodiment. Of course, the closing manners of both ends of the tube-like container, and the fixedly coupling manners of the upper end of rod with the upper end portion of the tube-like container can have various equivalent changes and combinations, for example, the fusion seal of the upper end portion of the tube-like container in the seventh embodiment (see FIG. 10) can be changed to mechanical seal and the like (such as inserting the rubber plug into the upper end opening of the tube-like container); and further the upper end of rod and the upper end portion of the tube-like container can be fixedly coupled together through mechanical connection and the like instead of integral fusion.

The second to fifth preparing methods correspond to several representative technical solutions of the invention, and the preparing methods corresponding to other technical solutions can be selected with reference to them. The making materials of the tube-like container described in the invention need to have good thermoplastic property, and the high molecule materials such as polyethylene, polypropylene, PET and etc are suitable; the length of the tube-like container is preferably from 40 mm to 200 mm, the outer diameter is preferably from 5 mm to 15 mm, and the wall thickness is preferably from 0.5 mm to 2 mm; the easy break-off mark cut by a cutter on the tube wall preferably has a depth of 0.1 mm to 0.5 mm and a length around the whole circumference, so that the tube-like container can be broken off easily along the easy break-off mark on the tube wall in any direction, and further the broken opening is smooth and has no sharp corner to make the use more convenient and safer; the easy break-off mark on the tube wall also can be obtained by a mold when the tube-like container is injection-molded, or can be obtained by changing the performances such as fragility of the partial material of the tube-like container.

To sum up, the wiper provided by the invention integrates delicately the rod, the wiping body provided at one end of the rod, the tube-like container and its unclosing manner into a unit, which is firm, airtight and capable of being opened easily, can be used safely and regularly anywhere, facilitates aseptic manipulation, can be used and stored conveniently, has simple preparing methods and can satisfies different technology requirements, has low production cost, and can be applied widely. The tube-like container and the rod can be made selectively of same thermoplastic material such as high molecule materials, and also can be made selectively of different thermoplastic materials having proper fusion temperatures, and the rod can employ materials having good elasticity, such as bamboo rod, wood rod and the like; the tube-like container and the rod can also have different colors, so that in the case that one end of the rod is fixedly coupled with an end of the tube-like container through fusion, the color of the rod can be exposed from the closed end to facilitate recognition in production and use; for the carried working fluid such as liquid medicine, disinfectant, liquid cosmetics, washing liquid and the like, as well as various working powder like substance, ointment like substance, oil like substance, glue and the like, reasonable technical solutions can be selected according to the characteristics of working substances themselves and the market requirements; and also in the technical solutions of the fourth and thirteenth embodiments, other wound protecting materials such as bandages can be placed into the tube-like container, to make the consumers feel more convenient. Since the bandages and other materials are deformable, the normal use of the tube-like container (breaking off) is not affected even though these kind of related articles are placed into its cavity. Also by extruding, injection-molding or other technologies, on the outer wall of the tube-like container there is simultaneously provided with an rectangular-shape independent chamber which is formed integrally therewith for storing bandages and other wound protecting materials. The opening end of the independent chamber and the opening end of the tube-like container can be closed simultaneously, and the easy break-off mark of the independent chamber and the easy break-off mark on the tube-like container can be on the same level and connected with each other, so that they can be broken off simultaneously. On the outer wall of the tube-like container there are also printed with easy break-off mark, product name, production date and the like by spraying code, thermo-transferring, displacing printing, screen printing, and other technologies, and certain number of wipers may be stored in board paper boxes or package bags made of compound films, to facilitate storage and transportation, and use. The wiper provided by the invention not only can be used in medical treatment, but also can be applied widely in daily life, for example, the wiper provided with detergents can be conveniently used to clean recording magnetic heads, CD drives of computers, and other elements or devices.

It needs to be noted that the preferred embodiments of the invention are not limited to those listed above, and the embodiments having various changes within the claims are all within the scope claimed by the invention; and the high molecule materials selected and used by the invention need to have good thermoplastic property, and various compound materials can be selected and used, which are intended to improve the tenacity, air tightness, environment protection, and other performances and are obtained by changing components, co-extruding multilayer, coating, secondary injection-molding and other technologies. It further needs to be explained that in the preferred embodiments listed by the invention, the ends of the tube-like container are closed mostly by using fusion manners, and both the reliability of the seal and the reasonability of the production technology are obvious. If the mechanical seal manner is applied, it is preferred that the related members are made by injection-molding technology, since the results of the mechanical seal are greatly affected by machining accuracy and assembling quality. Of course, the specific seal manners for closing the end opening of the tube-like container cannot be listed one by one in the invention. Further, the outer configurations of the tube-like container also can be changed widely, with their purpose and substantive effects remain unchanged. Such alternative equivalent solutions are all within the scope claimed by the invention.

While illustrative embodiments have been illustrated and described, it will be appreciated that various changes can be made therein without departing from the spirit and scope of the invention.

The invention claimed is:
1. A wiper, comprising:
a rod having a first end and a second end, a wiping body provided at the first end of the rod, and an outer packing, characterized in that said outer packing is a single-piece, elongate, tube-like container made of a high molecular mass polymer material having a uniform transverse cross section, the tube-like container having a first end and a second end;
wherein both the first end and the second end of the elongate tube-like container are fused themselves, respectively, to be closed permanently so as to form a rigid and integral tube-like container without any mechanical fit;
wherein the tube-like container is configured such that it can contain a substance selected from the group consisting of a working fluid, a working powder, and a working ointment;
wherein a tip of the second end of the rod is directly fused to, and thus fixedly coupled with, the first end of the tube-like container without any mechanical fit therebetween;
wherein the tube-like container has a circumferential easy break-off mark on an exterior surface of the tube-like container positioned, in the longitudinal direction, in the middle of the tube-like container, and the circumferen- tial easy break-off mark is away from the wiping body in the longitudinal direction of the tube-like container;

wherein the easy break-off mark is scored on an outer surface of the tube-like container around the circumference of the tube-like container by a cutting tool, wherein the easy break-off mark comprises a sharp cutting edge which is configured to induce an intense stress concentration effect on the easy break-off mark enough to break off the tube-like container of high molecular mass polymer material when a user grasps the two ends of the tube-like container and bends it slightly by force and thus the tube-like container is subjected to a rupturing force;

wherein the tube-like container is configured to be ruptured and separable into a first portion and a second portion along the easy break-off mark, and wherein the ruptured tube-like container will not reseal;

wherein the second end of the rod extends longitudinally from the first end of the tube-like container to beyond the position of the easy break-off mark;

wherein the tube-like container is configured such that, when broken off along the easy break-off mark, the first portion of the tube-like container is separable from the second portion of the tube-like container to expose the wiping body for wiping; and wherein the wiping body is near or in contact with an inner wall of the tube-like container circumferentially, and the wiping body abuts against the inner wall of the tube-like container when the tube-like container is broken off along the easy break-off mark, thus a flexible deformation of the rod occurs under force without interfering with the breaking-off of the tube-like container and the flexible deformation of the rod is constrained by the inner wall of the tube-like container, and the rod is configured to recover from the flexible deformation after said force that makes it deform is removed.

2. The wiper according to claim 1, characterized in that said wiping body provided at the first end of the rod is divided into two parts along the axial direction of the rod.

3. A wiper, consisting of:

a rod having a first end and a second end, a wiping body provided at the first end of the rod, and an outer packing, characterized in that said outer packing is a single-piece, elongate, tube-like container made of a high molecular mass polymer material having a uniform transverse cross section, the tube-like container having a first end and a second end;

wherein both the first end and the second end of the elongate tube-like container are fused themselves, respectively, to be closed permanently so as to form a rigid and integral tube-like container without any mechanical fit;

wherein the tube-like container is configured such that it can contain a substance selected from the group consisting of a working fluid, a working powder, and a working ointment;

wherein a tip of the second end of the rod is directly fused to, and thus fixedly coupled with, the first end of the tube-like container without any mechanical fit therebetween;

wherein the tube-like container has a circumferential easy break-off mark on an exterior surface of the tube-like container positioned, in the longitudinal direction, in the middle of the tube-like container, and the circumferential easy break-off mark is away from the wiping body in the longitudinal direction of the tube-like container;

wherein the easy break-off mark is scored on an outer surface of the tube-like container around the circumference of the tube-like container by a cutting tool, wherein the easy break-off mark comprises a sharp cutting edge which is configured to induce an intense stress concentration effect on the easy break-off mark enough to break off the tube-like container of high molecular mass polymer material when a user grasps the two ends of the tube-like container and bends it slightly by force and thus the tube-like container is subjected to a rupturing force;

wherein the tube-like container is configured to be ruptured and separable into a first portion and a second portion along the easy break-off mark, and wherein the ruptured tube-like container will not reseal;

wherein the second end of the rod extends longitudinally from the first end of the tube-like container to beyond the position of the easy break-off mark;

wherein the tube-like container is configured such that, when broken off along the easy break-off mark, the first portion of the tube-like container is separable from the second portion of the tube-like container to expose the wiping body for wiping; and wherein the wiping body is near or in contact with an inner wall of the tube-like container circumferentially, and the wiping body abuts against the inner wall of the tube-like container when the tube-like container is broken off along the easy break-off mark, thus a flexible deformation of the rod occurs under force without interfering with the breaking-off of the tube-like container and the flexible deformation of the rod is constrained by the inner wall of the tube-like container, and the rod is configured to recover from the flexible deformation after said force that makes it deform is removed.

4. The wiper according to claim 3, characterized in that said wiping body provided at the first end of the rod is divided into two parts along the axial direction of the rod.

* * * * *